United States Patent [19]
Ikekawa et al.

[11] Patent Number: 4,761,477
[45] Date of Patent: Aug. 2, 1988

[54] 13-PROPYLBERBERINE SALTS

[75] Inventors: Tetsuro Ikekawa, Chiba; Fumitake Shimada, Kasukabe; Jong-Chol Cyong, Akishima; Kazuo Uebaba, Yokohama, all of Japan

[73] Assignee: SS Pharmaceutical Co., Ltd., Tokyo, Japan

[21] Appl. No.: 802,447

[22] Filed: Nov. 27, 1985

[30] Foreign Application Priority Data

Nov. 29, 1984 [JP] Japan ................. 59-252425

[51] Int. Cl.⁴ .................. C07D 455/03; A61K 31/47
[52] U.S. Cl. ....................................................... 546/48
[58] Field of Search .......................... 546/48; 514/280

[56] References Cited

U.S. PATENT DOCUMENTS

3,910,938 10/1975 Ikekawa et al. ........................ 546/48

FOREIGN PATENT DOCUMENTS

| 184118 | 6/1986 | European Pat. Off. ............... 546/48 |
| 2403572 | 8/1974 | Fed. Rep. of Germany . |
| 2208659 | 6/1974 | France . |
| 1491358 | 11/1977 | United Kingdom . |

OTHER PUBLICATIONS

Shimada, et al., Chemical Abstracts, vol. 81, 91778w (1974).
Naruto, et al., Chemical Abstracts, vol. 77, 114605w (1972).
Kovar, et al., Chemical Abstracts, vol. 92, 89957n (1980).
Mikes, et al., Chemical Abstracts, vol. 94, 60915c (1981).
Sawa, et al., Chemical Abstracts, vol. 83, 114717h (1975).
Tolkachev, et al., Chemical Abstracts, vol. 88, 164809p (1978).
Huang, et al., Chemical Abstracts, vol. 94, 20341f (1981).
Nakamura, et al., Chemical Abstracts, vol. 86, 195207d (1977).
The Merck Index, 8th ed., Published by Merck & Co., Inc., Rahway, N. J., pp. 142-143, entry "Berberine", (1968).
The Pharmacopoeia of Japan, 10 ed., English Version, Soc. of Japanese Pharmacopoeia, Yakuji Nippo, Ltd., pp. 1-7 (1982).

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

A 13-propylberberine salt, which is represented by the following general formula (I):

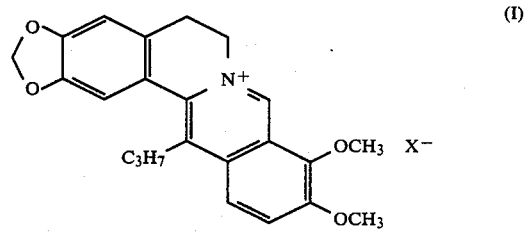

wherein $X^-$ means $HSO_4$ or $H_2PO_4$, has strong inhibitory effect against secretion, good stability and high water solubility. Its effects are shown promptly after its oral administration.

1 Claim, No Drawings

13-PROPYLBERBERINE SALTS

BACKGROUND OF THE INVENTION

1. Field of the Invention

This invention relates to novel salts of a berberine derivative, which salts are useful as drugs, and more specifically to 13-propylberberine salts represented by the following general formula (I):

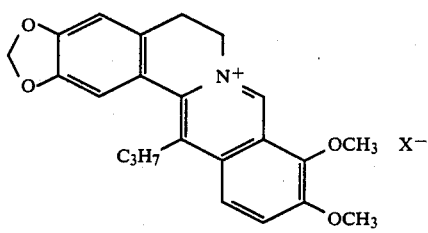

wherein $X^-$ means $HSO_4$ or $H_2PO_4$.

2. Description of the Prior Art

Berberine is a component of coptis rhizome, phellodendron bark and the like and is now used widely as drugs for controlling intestinal function. On the other hand, numerous berberine derivatives have also been known, but none of them are satisfactory in view of their efficacy as drugs.

As salts of 13-propylberberine, its halides such as iodide and bromide have conventionally been known. However, all of these salts are soluble only slightly in water and have poor stability. They are thus unsuitable as drugs.

SUMMARY OF THE INVENTION

The present inventors have carried out a variety of researches. As a result, it has been found that 13-propylberberine sulfate or phosphate is extremely stable compared with the above-described halides and is readily soluble in water, and exhibits excellent drug efficacy, leading to completion of the present invention.

In one aspect of this invention, there is thus provided a 13-propylberberine salt represented by the following general formula (I):

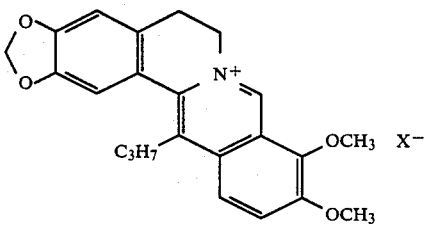

wherein $X^-$ means $HSO_4$ or $H_2PO_4$.

The 13-propylberberine salt is useful as a drug for controlling intestinal function or an antidiarrheic owing to its strong inhibitory effect against secretion, good stability and high water solubility. Its effects are shown promptly after its oral administration.

The above and other objects, features and advantages of the present invention will become apparent from the following description and the appended claims.

DETAILED DESCRIPTION OF THE INVENTION

The compound of this invention may be obtained, for example, by preparing basic 13-propylberberine and then adding an equimolar amount of sulfuric acid or phosphoric acid thereto, both, in a manner known per se in the art.

More specifically, basic 13-propylberberine may be prepared usually by causing a propyl halide to act on acetone berberine or by causing an allyl halide to act on acetone berberine and then reducing the allyl group.

The sulfuric or phosphoric acid addition salt of 13-propylberberine may be prepared by adding a solution of an equimolar amount or more of sulfuric acid or phosphoric acid in a suitable solvent such as methylene chloride, methanol or ethanol to basic 13-propylberberine and after optionally heating the resultant mixture to dissolve the basic 13-propylberberine if needed, adding a bad solvent such as ethyl ether or chloroform suitably to the solution and collecting precipitated crystals or distilling off the solvent to convert the resultant salt into crystals.

[Effects, and Advantages of the Invention]

(1) Antidiarrheic effect:

The antidiarrheic effect of the compound of this invention was tested in accordance with the following method. Results are shown in Table 1.

(Testing method)

An experiment was conducted by the method proposed by M. Sabir et al [Ind. J. Med. Res. 65, 303 (1977)].

Namely, SPF male Wister rats of 6–7 weeks old, three rats per group, were fasted for 72 hours. Under sodium pentobarbital anesthesia, they were each subjected to laparotomy, followed by ligation at the beginning of the jejunum and at the end of the ileum. One of the test compounds and 20 μg of cholera toxin were injected in the ligated tract and 5 hours later, the amount of secreta was measured. Besides, a control injected only with cholera Toxin was also provided to calculate inhibition rates (%).

TABLE 1

| Test compound | Injected amount (mg/kg) | Inhibition rate (%) |
|---|---|---|
| Berberine chloride | 20 | 8.0 |
| 13-Propylberberine bisulfate | 2 | 40.0 |
| 13-Propylberberine bisulfate | 0.5 | 13.0 |

As shown in the above table, the compound of this invention has an extremely-stronger inhibitory effect against secretion compared with berberine chloride which has conventionally been known to control diarrhea.

(2) Stability:

Test compounds were heated at 100° C. for 8 hours. Changes in their appearance and their percent remainders were studied. Results are shown in Table 2.

TABLE 2

| Test compound | Changes in appearance | Percent remainder (%) |
|---|---|---|
| 13-Propylberberine bisulfate | no changes | 100.0 |
| 13-Propylberberine | no changes | 99.8 |

TABLE 2-continued

| Test compound | Changes in appearance | Percent remainder (%) |
| --- | --- | --- |
| primary phosphate | | |
| 13-Propylberberine chloride | turned to brown | 48.7 |
| 13-Propylberberine bromide | turned to brown | 57.0 |
| 13-Propylberberine iodide | turned to brown | 52.1 |

As shown in the above table, the bisulfate and primary phosphate of this invention are extremely stable compared with the conventionally-known halides.

(3) Solubility in water:

Results are shown in Table 3.

TABLE 3

| Test compound | Solubility |
| --- | --- |
| 13-Propylberberine bisulfate | soluble |
| 13-Propylberberine primary phosphate | soluble |
| 13-Propylberberine chloride | slightly soluble |
| 13-Propylberberine bromide | slightly soluble |
| 13-Propylberberine iodide | slightly soluble |

As readily envisaged from the above table, the compounds of this invention have such advantages that compared with the conventionally-known halides, both of them have high water solubilities and their effects are shown promptly after their oral administration.

The manner of administration and dosage of the compounds of this invention will next be described.

Regarding the manner of their administration, it is preferable to administer them orally in such preparation forms as tablets, capsules, granules, syrup and the like.

Their oral preparations such as their tablets, capsules, granules and the like may be produced by formulating them suitably in combination with a excipient such as starch, lactose or mannitol, a binder such as sodium carboxymethylcellulose or hydroxypropyl cellulose, a disintegrator such as crystalline cellulose or calcium carboxymethylcellulose, a lubricant such as talc or magnesium stearate, a fluidity improver such as light silicic anhydride and the like.

As to their dosage, it is ordinarily suitable to administer 0.01–10 mg/Kg.administration 2–3 times a day in the case of an adult.

The compounds of this invention can also be used advantageously as biochemical reagents and the like owing to their strong inhibitory effects against the activity of adenylate cyclase.

[EXAMPLES]

The present invention will next be described by the following Examples and Referential Examples.

Referential Example 1

Five grams of acetone berberine were provided, followed by an addition of 50 ml of chloroform to dissolve the acetone berberine. Then, 10 ml of allyl bromide was added. After fitting a reflux condenser, the resultant mixture was refluxed for 7 hours. After distilling any excess allyl bromide off together with the solvent, to the residue 50 ml of methylene chloride was added and the precipitated yellow crystals were filtered off. The filtrate was concentrated, followed by an addition of a small amount of ethyl ether. Subsequent to collection of the precipitated yellow crystals by filtration, the crystals were washed with a small amount of a mixed solution of chloroform and ethyl ether and were then dried to obtain 2.81 g of 13-allylberberine bromide.

Thereafter, 1.5 g of the above-prepared 13-allylberberine was dissolved in 40 ml of ethanol, followed by an addition of 1.5 g of 10% Pd-C. The 13-allylberberine was then catalytically reduced by passing hydrogen gas through the liquid mixture. After completion of the reaction, the catalyst was filtered off and the filtrate was concentrated. The precipitated yellow crystals were then collected by filtration. Thereafter, they were washed with a mixed solvent of chloroform and ethyl ether and dried to obtain 1.4 g of 13-propylberberine bromide.

EXAMPLE 1

After adding 5 ml of methylene chloride and 1 ml of methanol to 0.3 g of 13-propylberberine and dissolving the latter, 2 ml of a 5% sulfuric acid solution in methanol was added. After adding ethyl ether until right before precipitation of crystals, the resultant solution was allowed to stand overnight. The precipitated yellow crystals were collected by filtration. The crystals were then washed with a small amount of a mixed solution of chloroform and ethyl ether, followed by their drying under reduced pressure to obtain 0.14 g of 13-propylberberine bisulfate.

Melting point: 239°–241° C.

Elementary analysis (%): Calculated for $C_{23}H_{25}NO_8S$ (475.51): C, 58.10; H, 5.30; N, 2.95. Found: C, 57.86; H, 5.52; N, 2.97.

EXAMPLE 2

After adding 5 ml of methylene chloride and 1 ml of methanol to 0.3 g of 13-propylberberine and dissolving the latter, 2 ml of a 5% phosphoric acid solution in methanol was added. After adding ethyl ether until right before precipitation of crystals, the resultant solution was allowed to stand overnight. The precipitated yellow crystals were collected by filtration.

The crystals were then washed with a small amount of a mixed solution of chloroform and ethyl ether, followed by their drying under reduced pressure to obtain 0.13 g of 13-propylberberine primary phosphate.

Melting point: 219°–221° C.

Elementary analysis (%): Calculated for $C_{23}H_{26}NO_8P$ (475.43): C, 58.11; H, 5.51; N, 2.95. Found: C, 58.02; H, 5.66; N, 2.91.

REFERENTIAL EXAMPLE 2

(Tablet)

| | |
| --- | --- |
| 13-Propylberberine bisulfate | 50 mg |
| D-Mannitol | 200 mg |
| Crystalline cellulose | 50 mg |
| Potato starch | 28 mg |
| Calcium carboxymethylcellulose | 16 mg |
| Talc | 4 mg |
| Magnesium stearate | 2 mg |
| Total | 350 mg |

The above components in the above amounts were mixed, from which a single piece of tablet was prepared in a usual manner.

REFERENTIAL EXAMPLE 3

(Capsule)

| | |
|---|---|
| 13-Propylberberine primary phosphate | 25 mg |
| Crystalline cellulose | 17 mg |
| Light silicic anhydride | 7 mg |
| Magnesium stearate | 1 mg |
| Lactose | 130 mg |
| Total | 180 mg |

The above components in the above amounts were mixed, from which granules were prepared in a usual manner. They were then filled in a single piece of No. 3 capsule to obtain a capsule.

REFERENTIAL EXAMPLE 4

(Reagent for biochemical field)

At 200 nM concentration, 13-propylberberin bisulfate inhibits about 50% of adenylate cyclase activity of intestinal epithetial cells or splenic lymphocytes in mice.

Having now fully described the invention, it will be apparent to one of ordinary skill in the art that many changes and modifications can be made thereto without departing from the spirit or scope of the present invention as set forth herein.

I claim:

1. A 13-propylberberine salt represented by the following general formula (I):

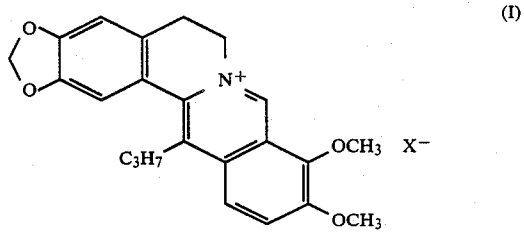

wherein $X^-$ means $HSO_4$ or $H_2PO_4$.

* * * * *